United States Patent [19]
Pech et al.

[11] Patent Number: 5,812,397
[45] Date of Patent: Sep. 22, 1998

[54] APPARATUS FOR TECHNICAL DIAGNOSIS OF ERRORS IN A MEDICAL/DENTAL APPARATUS

[75] Inventors: Guenther Pech; Josef Pabst, both of Heddesheim, Germany

[73] Assignee: Sirona Dental Systems GmbH & Co. KG, Bensheim, Germany

[21] Appl. No.: 510,313

[22] Filed: Aug. 2, 1995

[30] Foreign Application Priority Data

Aug. 4, 1994 [EP] European Pat. Off. .............. 94112233

[51] Int. Cl.$^6$ .................................................. G06K 15/18
[52] U.S. Cl. .................... 364/186; 364/580; 371/22.1; 371/22.6; 128/713
[58] Field of Search ..................................... 364/580, 481, 364/DIG. 1, 186; 371/22.1, 20.1, 22.6; 324/503, 73.1

[56] References Cited

U.S. PATENT DOCUMENTS

| 4,868,826 | 9/1989 | Smith et al. .............................. 371/9.1 |
| 4,907,230 | 3/1990 | Heller et al. ............................ 371/22.1 |
| 5,300,926 | 4/1994 | Stoeckl .................................... 345/157 |

FOREIGN PATENT DOCUMENTS

| 0140822 | 5/1985 | European Pat. Off. . |
| 0304848 | 3/1989 | European Pat. Off. . |
| 0455852 | 11/1991 | European Pat. Off. . |

*Primary Examiner*—James P. Trammell
*Assistant Examiner*—Shah Kaminis
*Attorney, Agent, or Firm*—Hill & Simpson

[57] ABSTRACT

An apparatus having a plurality of components with printed circuit boards (PCB) having electronic circuits that act on electrical and/or electromechanical function elements is provided. The PCBs communicate with one another via a serial communication bus. The components have analog and digital signal generators allocated to them whose signals act on the PCBs as an input quantity. The PCBs have the capability for implementing self-tests. The self-tests provide test results that are supplied to a service computer as input quantities. Converters for the data for a transmission via a standard interface are provided for the transmission of the data onto the service computer. In an embodiment, the service computer has a first module with a diagnosis software component that enables an interactive error diagnosis off-line. The service computer also contains a second module that produces a connection between the first module and the apparatus components to enable an on-line diagnosis with the first module. The second module contains a logic element that logically operates the test results with one another and leads to a diagnosis result that, given adequate localization, appears on a display. When the displayed diagnosis is not yet exact enough, the test results are returned to the first module and interactively further-processed. Interactively supplied answers flow back into the logic element and are operated therein again until an unambiguous error diagnosis results.

8 Claims, 3 Drawing Sheets

| status-information | equipment module | | | | | | |
|---|---|---|---|---|---|---|---|
| | 1 | 2 | 3 | 4 | 6 | 8 | 9 |
| supply voltage 24V error | 0 | [1] | [1] | 0 | [1] | 0 | 0 |
| supply voltage 16V error | [1] | 0 | 0 | 0 | 0 | 0 | 0 |
| operating pressure 1.5 bar e or | 0 | 0 | 0 | 0 | 0 | [1] | 0 |
| status of functional element 16' (eg rotational speed error) | [1] | 0 | 0 | 0 | 0 | 0 | 0 |
| status of functional element 16" (eg temperature error) | 0 | 0 | 0 | 0 | 0 | [1] | 0 |

1 = error
0 = no error
[ ] = error combinations

APPARATUS FOR TECHNICAL DIAGNOSIS OF ERRORS IN A MEDICAL/DENTAL APPARATUS

BACKGROUND OF THE INVENTION

1. Field of the Invention

The invention is directed generally to diagnostic equipment and more specifically to an apparatus for the technical diagnosis of errors in a medical or dental apparatus.

2. Description of the Related Art

Medical devices, particularly dental systems, usually comprise a multitude of apparatus components that contain one or more flat modules with electronic circuits that interact with electrical and/or electromechanical function elements. In a dental apparatus for example, such individual components can be a patient bearing chair, a dentist's or dental assistant's element, brackets for holding and adjusting the two elements, a water unit having devices for rinsing and suctioning, as well as for water preparation, a foot control means with which, among other things, the function elements can be driven, as well as a junction box in which a supply unit and various valves for air and water are accommodated.

Given the plethora of possibilities, it is difficult for the service technician to quickly find and eliminate errors, faults, malfunctions and the like. When, for example, the electrical drill drive malfunctions or does not function at all, a number of errors can be responsible for the problem. As the most obvious cause, the motor in the handpiece itself may be malfunctioning; however, the input voltage in the junction box or some other, intervening fault can be the cause of the malfunction. As a result of the electrical linking of the apparatus components, the cause of the malfunction of the motor can also lie in certain component parts that are not directly connected to the motor.

A need, therefore, has arisen for an apparatus for performing a non-invasive technical diagnosis of errors in a medical/dental apparatus.

SUMMARY OF THE INVENTION

It is, therefore, an object of the present invention to provide a diagnostic apparatus for localizing faults without an inconvenient and time-consuming search which, in previous approaches, usually involved dismantling the apparatus components.

This and other objects are achieved in an apparatus for diagnosing errors in a medical/dental apparatus, comprising: a medical/dental station having a plurality of components that contain printed circuit boards (PCB) with electronic circuits that act on electrical and/or electromechanical function elements, wherein the PCBs communicate with one another via a serial communication bus, and the plurality of components have analog and digital signal generators allocated thereto to generate signals that act on the PCBs as an input quantity; means for implementing self-tests located in the PCBs, the self-tests testing voltages on the PCBs and functions of internal circuits as well as parties on the communication bus to supply test results to a service computer as input quantities; a first module capable enabling an off-line interactive error diagnosis in the service computer; a second module producing a connection between the first module and the plurality of components and capable of enabling an on-line diagnosis with the first module, the second module containing a logic element to out logically operate the test results with one another to provide a diagnostic result.

In an advantageous embodiment of the present invention, a service computer can be an integral component part of the apparatus and can be allocated to one of the apparatus components. It can also be an advantage of the present invention to arrange the service computer externally of the apparatus components.

An exemplary embodiment of the invention is set forth in greater detail below with reference to the figures.

DETAILED DESCRIPTION OF THE PREFERRED EMBODIMENTS

Figure 1:
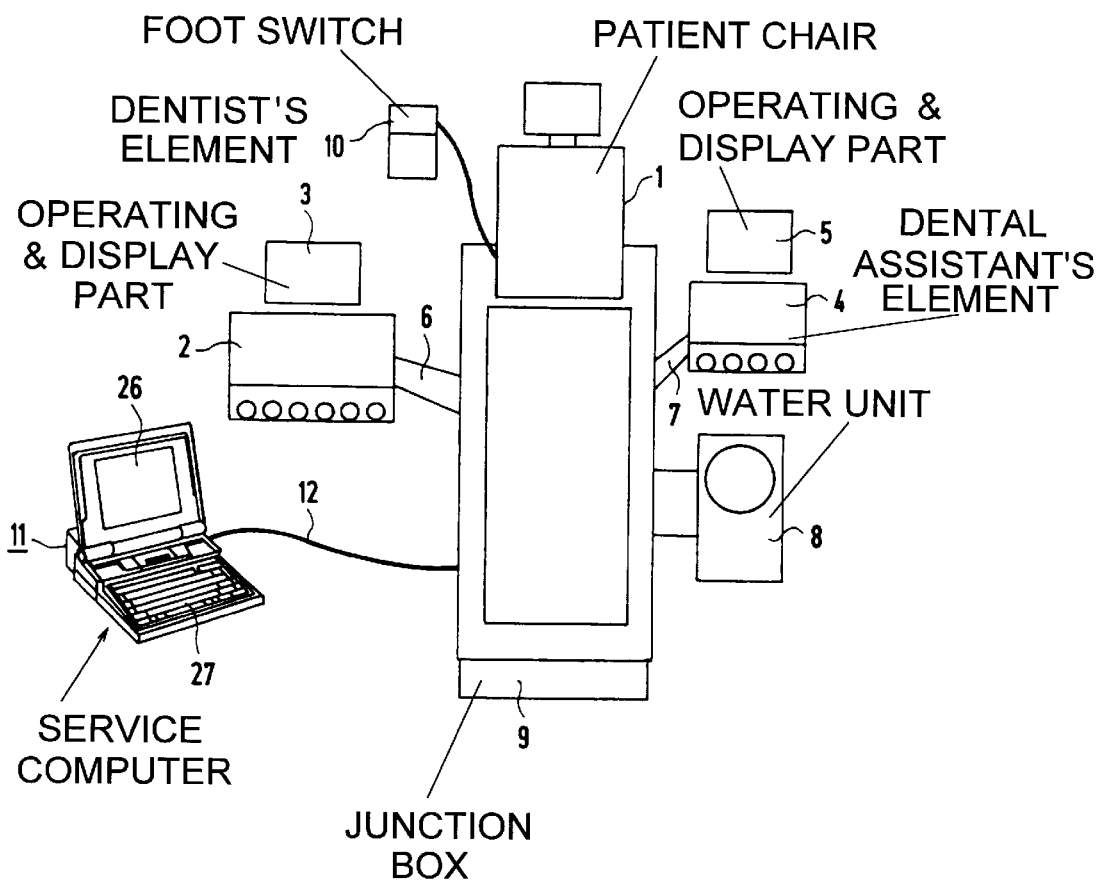
FIG. 1 is a plan view of a dental workstation in which an embodiment of the present invention can be utilized.

In a simplified illustration, FIG. 1 shows a plan view of a dental workstation that contains the following individual apparatus components: a patient chair 1, a dentist's element 2 having an operating and display part 3, a dental assistant's element 4 having an operating and display part 5, brackets 6 and for the afore-mentioned elements 2 and 4, a water unit 8, a junction box 9 and a foot switch 10.

A service computer 11 is shown in FIG. 1. The service computer 11 can be a lap top computer and is connected to the apparatus components via a cable 12. Instead of the lap top shown in FIG. 1, a PC or some other, suitable computer (notebook, palm top) can also be provided as the service computer 11.

Figures 2, 4:
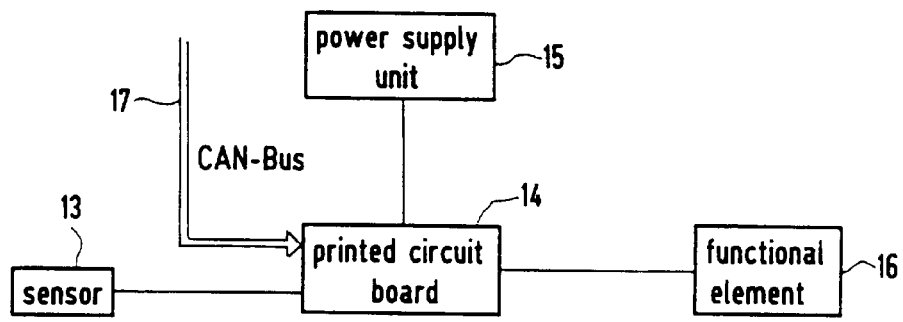
FIG. 2 is a schematic illustration of the linkage of elements of an embodiment of the present invention.
FIG. 4 is a tabular representation of status information of dental equipment moduls used in accordance with the principles of an embodiment of the present invention.

As shown in FIG. 2, at least some of the apparatus components 1–10 respectively contain at least one printed circuit board 14 (PCB) with electronic circuits that can interact with electrical and/or electromechanical function elements 16. Electrical function elements 16, for example, can be a display unit or illumination elements or ultrasonic scaler and/or high-frequency surgery modules. Electromechanical function elements can be electrical motors and/or solenoid valves. Electric motors can be provided as drives as well as in dental instruments; they can also be arranged as adjustment motors in the apparatus components 1, 2 and 4, as well as 6 and 7.

Analog and digital sensors 13 (see FIG. 2) that act as signal generators and supply status information from the function elements 16 are allocated to the individual apparatus components. Examples of such status information include the status of switches, the presence of voltages, temperatures or pressure, as well as the adherence to predetermined thresholds.

FIG. 2 shows the linkage of these elements in a schematic illustration. The sensor 13 is connected to the PCB 14 and supplies a corresponding status signal to the latter. The flat module 14, which is supplied with the necessary voltage by a power supply unit 15, activates the appertaining function element 16. For example, the function element 16 can be a control valve or an electric drive motor.

Figure 3:
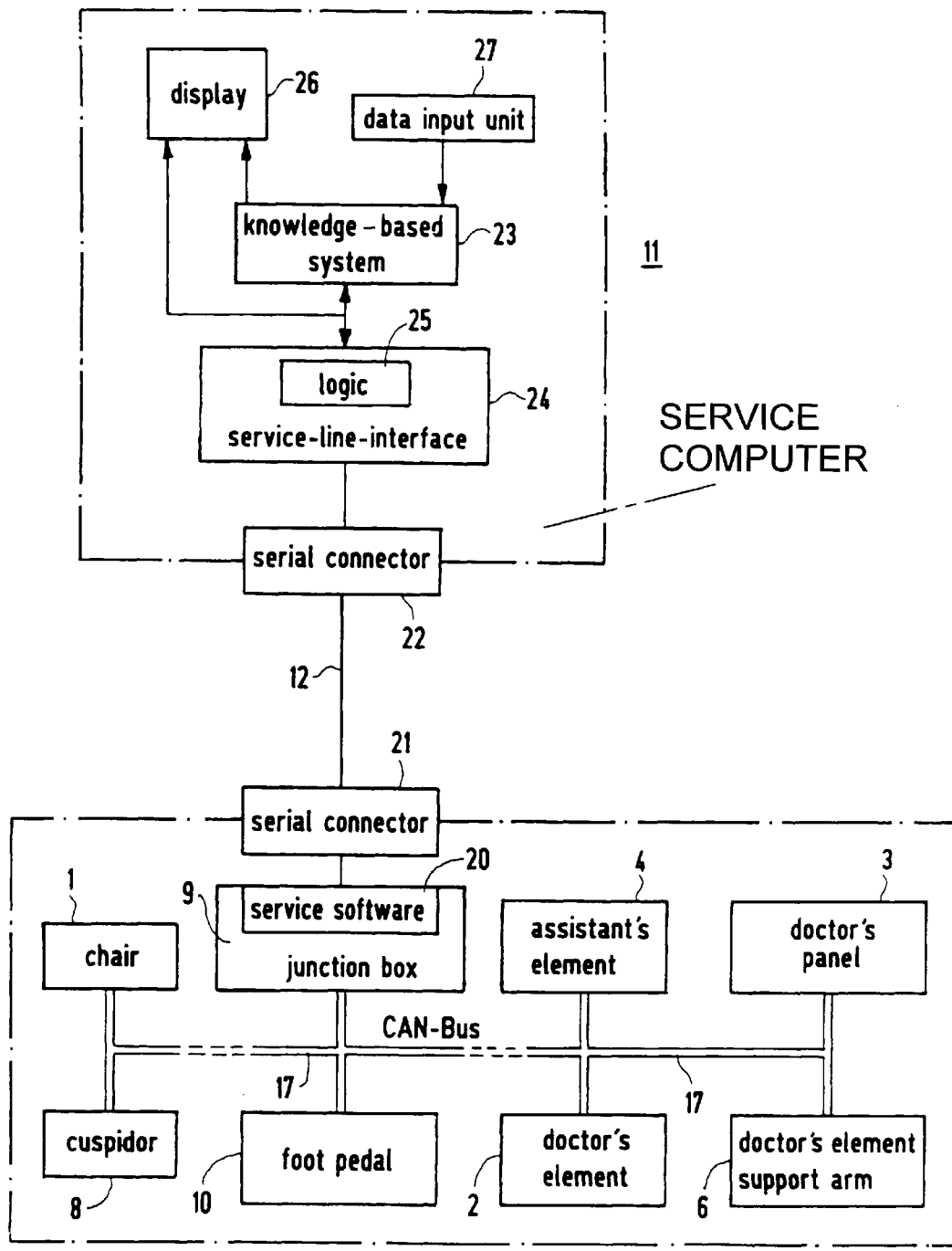
FIG. 3 is a block diagram of an apparatus of an embodiment of the present invention.

FIG. 3 shows that all PCBs 14 communicate with one another via a serial communication bus 17. It is assumed in the exemplary embodiment that not all individual apparatus components 1–10 but only the components 1–4,6,8 and 9 that include PCBs 14 that act on electrical and/or electromechanical function elements 16 are connected to one another via the communication bus 17.

The apparatus of the present invention contains a specific service software 20 whose module is expediently accommodated in the junction or terminal box 9 (FIG. 3). This service software 20 serves the purpose of converting the data that are important for the diagnosis for transmission via the serial standard interface. A communication with any arbitrary computer that has a serial interface is thus possible via the connecting cable 12 and suitable connecting plugs 21,22.

The service computer 11 contains a first module 23 having a diagnosis software component that contains a commercial error-searching system (for example, Diagnostic Advisor of Emerald Intelligence, USA). This commercial error-searching system is a knowledge-based system for an interactive error search. It works on the basis of the conducted, interactive diagnosis, i.e. the user must answer questions according to the knowledge previously input by experts, namely without utilizing the apparatus status/error information in on-line operation.

A second module 24 that contains a logic element 25 is connected to the first module 23. The second module 24 translates service instructions that are input in the first module 23 by technical experts into a corresponding command for the apparatus components and transmits this command via the serial standard interface 12 to the apparatus components to be diagnosed. The status and error data returned from these apparatus components are read into the afore-mentioned logic element 25 and are correspondingly edited by logical operation of the status/error data. Advantageously, the communication of the components ensues via a CAN bus command (Controlled Area Network).

The error diagnosis sequences in the following way. The PCBs 14 of the individual apparatus components 1–10 first carry out a self-test by testing the voltages of the rated voltages provided on the PCBs 14, as well as the functions of internal circuits and also check the parties at the communication bus 17 as to their presence and function with reference to the communication.

The self-tests on the PCBs 14 supply test results that are supplied to the service computer 11 as input quantities via the serial interface 12. The test results input into the computer 11 are logically operated with one another in the logic element 25. The logical operation proceeds according to a two-dimensional matrix set forth below in greater detail with reference to the example of FIG. 4.

The errors in the individual apparatus components 1–4 as well as 6,8 and 9 registered on the basis of the results of the self-test function are read into the logic element 25 and are operated via logical equations that are contained in the software component. The structure of these equations is based on the idea that an error or, respectively, a faulty function in an apparatus component is expressed in a specific error pattern, i.e. in the occurrence of a specific combination of errors.

In the exemplary embodiment of FIG. 4, a voltage error in the 24 volt supply voltage is reported to the diagnosis system, namely respectively by the components 2, 3 and 6, i.e. from the dentist's element 2, the dentist's operating and display part 3 and the dentist's bracket 6. Since the three components are physically directly connected to one another and form a unit, the probability is very high that there is not a line interruption of the 24 volt supply at all three components but that the central fuse in the supply area for the unit is burned out. The logical operation in the exemplary embodiment can thus be such that when a 24 V error is present at component 2 and a 24 V error is present at component 6 and a 24 V error is present at component 3, then the diagnosis is made that the central fuse is burned out. The diagnosis, for example, can appear encoded at the display 26 of the computer 11.

The advantage of the logical operation of these test results is that the voltage supply paths of the individual components in the illustrated example need not be checked in sequence before it is then ultimately found that the central fuse is blown.

Given an adequate localization of the error, a corresponding instruction is provided directly at the picture screen. When the error is not adequately localized, status information can be interrogated from function elements 16 of the individual apparatus components, for example solenoid valves, lamps or motors. The data then provide additional information for a diagnosis to be started again.

When an adequate localization of the error has not been established, even the diagnosis is interactively continued within the module 23. The answers interactively input via an input unit 27 (for example, a keyboard of the computer 11, see FIG. 1) flow back into the logic element 25 and are again operated upon therein until an unambiguous error diagnosis has been established. The interactively obtained information supplements the data already present and enters into the logical equation for the typical error pattern of the occurring error. This ultimately leads to a more exact localization of the error.

In addition to the afore-mentioned exemplary embodiment of an error diagnosis with an error source in the area of the 24 volt supply voltage, the analogous case applies to the logical operation of different types of errors, for example faulty status of switches, operating pressures, temperatures, etc., as indicated in FIG. 4. For example, an error message in the 16 volt operating voltage in the apparatus component 1 can be operated with a status report of a function element 16', for example with an error in the speed of a drive motor in the apparatus component 1. Likewise, an error message in the operating pressure of an agent in the water unit 8 can be operated with a temperature error message in this apparatus component.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. In a medical/dental station having a plurality of functional elements respectively operated by a plurality of printed circuit boards (PCBs), said PCBs being connected to each other via a serial communication bus, the improvement of an apparatus for diagnosing a source of an error causing a malfunctioning of at least one of said functional elements, comprising:

a plurality of self-test means respectively disposed in said PCBs for conducting an internal self-test of that PCB in which the self-test means is disposed, each self-test means conducting a self-test including at least one of testing a voltage on said PCB produced by interaction of the PCB with the functional element respectively connected thereto, testing functioning of an internal circuit in said PCB which occurs due to said interaction, and testing whether said PCB is properly communicating with said communication bus, each of said self-test means producing a self-test result dependent on the self-test conducted by the self-test means;

a first module including diagnostic means for conducting an on-line diagnostic routine for identifying said source, and including means for receiving status information describing malfunctioning of any of said functional elements; and a second module connected between said first module and said communication bus and including logic means, supplied with said test results from each of said PCBs and supplied with said status information from said first module, for logically linking said status information and said test results to form a logic result, and for supplying said logic result to said diagnostic means in said first module, said diagnostic means employing said logic result to identify said source using said diagnostic routine.

2. The improvement of claim 1 wherein said medical/dental station comprises a component containing at least one of said printed circuit boards, and wherein said first module comprises an integral part of said component.

3. The improvement of claim 1 wherein said medical/dental station comprises an operating and display component comprising at least one of said printed circuit boards, and wherein said first module comprises an integral part of said operating and display component.

4. The improvement of claim 1 further comprising a service computer remote and temporarily connectable to said communication bus, and wherein said first module comprises a component of said service computer.

5. The improvement of claim 4 further comprising a standard interface in communication with said communication bus, and wherein said service computer comprises a cable terminating in a plug connected to said standard interface.

6. The improvement of claim 1 further comprising display means, in communication with said first module, for displaying a diagnostic result containing an identification of said source.

7. In a medical/dental station having a plurality of functional elements respectively operated by a plurality of printed circuit boards (PCBs), said PCBs being connected to each other via a serial communication bus, a method for diagnosing a source of an error causing malfunctioning of at least one of said functional elements, said method comprising the steps of:

in each of said PCBs, conducting an internal self-test of that PCB, including at least one of testing a voltage on said PCB produced by interaction of the PCB with the functional element respectively connected thereto, testing functioning of an internal circuit in said PCB which occurs due to said interaction, and testing whether said PCB is properly communicating with said communication bus, said self-test producing a self-test result;

in a first module, conducting an on-line diagnostic routine and thereby identifying said source, and supplying status information to said first module describing malfunctioning of any of said functional elements; and establishing a communication between said first module and a second module and between said second module and said communication bus to supply said second module with said test results from each of said PCBs and with said status information from said first module;

in said second module, logically linking said status information and said test results to form a logic result; and supplying said logic result to said first module and in said first module conducting said diagnostic routine employing said logic result to identify said source.

8. A method as claimed in claim 7 comprising the additional steps of:

(a) displaying a diagnostic result identifying said source;

(b) if said diagnostic result does not satisfy an exactness criterion, repeating said diagnostic routine in said first module using said diagnostic result as a starting point; and (c) iteratively repeating steps (a) and (b) until said exactness criterion is satisfied.

\* \* \* \* \*